(12) United States Patent
Herman et al.

(10) Patent No.: US 11,786,706 B2
(45) Date of Patent: *Oct. 17, 2023

(54) MICRO-NEEDLE BLADDER BALLOON

(71) Applicant: Boston Scientific Scimed, Inc., Maple Grove, MN (US)

(72) Inventors: Carrie Lee Herman, Minnetonka, MN (US); Natalie Ann Borgos, Roseville, MN (US); Kari L. Cierzan, Minnetonka, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 452 days.

This patent is subject to a terminal disclaimer.

(21) Appl. No.: 16/783,600

(22) Filed: Feb. 6, 2020

(65) Prior Publication Data

US 2020/0171280 A1 Jun. 4, 2020

Related U.S. Application Data

(63) Continuation of application No. 13/993,752, filed as application No. PCT/US2011/065468 on Dec. 16, 2011, now Pat. No. 10,589,070.

(Continued)

(51) Int. Cl.
  *A61M 25/10* (2013.01)
  *A61M 37/00* (2006.01)
  *A61M 31/00* (2006.01)

(52) U.S. Cl.
  CPC .......... *A61M 25/10* (2013.01); *A61M 31/00* (2013.01); *A61M 37/0015* (2013.01);
  (Continued)

(58) Field of Classification Search
  CPC .... A61M 2025/1013; A61M 2025/105; A61M 2025/1086; A61M 2025/1072;
  (Continued)

(56) References Cited

U.S. PATENT DOCUMENTS 2,819,718 A 1/1958 Goldman et al.
2,936,760 A 5/1960 Gants
(Continued)

FOREIGN PATENT DOCUMENTS

EP 0363203 A2 4/1990
EP 0444831 A2 9/1991
(Continued)

OTHER PUBLICATIONS

Communication pursuant to Rule 71(3) EPC for European Application No. 11848939.2, dated Jun. 26, 2018, 31 pages.

(Continued)

*Primary Examiner* — Rebecca E Eisenberg
*Assistant Examiner* — Justin L Zamory
(74) *Attorney, Agent, or Firm* — Brake Hughes Bellermann LLP

(57) ABSTRACT

Devices and methods for delivering treatment fluids or particulates such as, stem cells, drugs, Botox and like, to an inner lining of a bladder for treatment of urinary tract disorders, including over-active bladder. A balloon delivery system can include an inflation balloon having a plurality of micro-needles configured to pierce and otherwise puncture an inner bladder wall so as to deliver the treatment fluid to bladder tissue. The treatment fluid can be directly injected into the bladder tissue using the micro needles. Alternatively, the micro needles can be fabricated of bioabsorbable or bioresorbable materials such that the micro needles can remain embedded within the bladder tissue to deliver the treatment fluid or particulate.

14 Claims, 9 Drawing Sheets

Related U.S. Application Data

(60) Provisional application No. 61/423,732, filed on Dec. 16, 2010.

(52) U.S. Cl.
CPC ............. A61M 2025/105 (2013.01); A61M 2025/1013 (2013.01); A61M 2025/1086 (2013.01); A61M 2037/003 (2013.01); A61M 2037/0023 (2013.01); A61M 2037/0046 (2013.01); A61M 2037/0061 (2013.01)

(58) Field of Classification Search
CPC .. A61M 2025/1075; A61M 2025/0093; A61M 37/0015; A61M 2037/0023; A61M 2037/003
See application file for complete search history.

(56) References Cited

U.S. PATENT DOCUMENTS

| | | |
|---|---|---|
| 4,444,188 A | 4/1984 | Bazell et al. |
| 4,456,011 A | 6/1984 | Warnecke |
| 4,573,966 A | 3/1986 | Weikl et al. |
| 4,610,662 A | 9/1986 | Weikl et al. |
| 4,636,195 A | 1/1987 | Wolinsky |
| 4,637,396 A | 1/1987 | Cook |
| 4,660,560 A | 4/1987 | Klein |
| 4,702,252 A | 10/1987 | Brooks et al. |
| 4,705,502 A | 11/1987 | Patel |
| 4,781,677 A | 11/1988 | Wilcox |
| 4,932,956 A | 6/1990 | Reddy et al. |
| 4,932,958 A | 6/1990 | Reddy et al. |
| 4,261,339 B1 | 9/1990 | Hanson et al. |
| 5,188,595 A | 2/1993 | Jacobi |
| 5,312,456 A | 5/1994 | Reed et al. |
| 5,344,397 A | 9/1994 | Heaven et al. |
| 5,421,826 A | 6/1995 | Crocker et al. |
| 5,549,555 A | 8/1996 | Sohn |
| 5,707,357 A | 1/1998 | Mikhail et al. |
| 5,810,767 A | 9/1998 | Klein |
| 5,868,776 A | 2/1999 | Wright |
| 6,083,166 A | 7/2000 | Holdaway et al. |
| 6,283,947 B1 | 9/2001 | Mirzaee |
| 6,364,855 B1 | 4/2002 | Zappala |
| 6,471,672 B1 | 10/2002 | Brown et al. |
| 6,529,011 B1 | 3/2003 | Okubo |
| 6,638,246 B1 * | 10/2003 | Naimark ............... A61M 25/10 604/103 |
| 6,719,709 B2 | 4/2004 | Whalen et al. |
| 6,743,211 B1 | 6/2004 | Prausnitz et al. |
| 6,863,654 B2 | 3/2005 | Zappala et al. |
| 7,001,405 B2 | 2/2006 | Kieturakis et al. |
| 7,220,252 B2 | 5/2007 | Shah |
| 7,338,468 B2 | 3/2008 | Freyman |
| 11,357,955 B2 | 6/2022 | Herman et al. |
| 2002/0173745 A1 | 11/2002 | Santini et al. |
| 2003/0153905 A1 | 8/2003 | Edwards et al. |
| 2004/0087995 A1 | 5/2004 | Copa et al. |
| 2004/0226556 A1 | 11/2004 | Deem et al. |
| 2005/0070938 A1 | 3/2005 | Copa et al. |
| 2005/0131269 A1 | 6/2005 | Talmadge |
| 2005/0131431 A1 | 6/2005 | Copa et al. |
| 2006/0058815 A1 | 3/2006 | Mickley et al. |
| 2006/0079836 A1 | 4/2006 | Holman et al. |
| 2006/0206122 A1 | 9/2006 | Copa et al. |
| 2006/0217680 A1 | 9/2006 | Barath |
| 2006/0264985 A1 | 11/2006 | Copa et al. |
| 2006/0276811 A1 | 12/2006 | Copa et al. |
| 2007/0219584 A1 | 9/2007 | Copa et al. |
| 2008/0051723 A1 | 2/2008 | Laermer et al. |
| 2008/0108959 A1 | 5/2008 | Jung et al. |
| 2009/0187167 A1 * | 7/2009 | Sexton ............... A61B 17/205 600/583 |
| 2009/0227949 A1 | 9/2009 | Knapp et al. |
| 2009/0240199 A1 | 9/2009 | Rahimsobhani et al. |
| 2009/0254064 A1 | 10/2009 | Boatman |
| 2010/0076401 A1 | 3/2010 | Von Oepen et al. |
| 2011/0166516 A1 * | 7/2011 | Orr ..................... A61M 25/104 604/103.01 |
| 2013/0331783 A1 | 12/2013 | Herman et al. |

FOREIGN PATENT DOCUMENTS

| | | |
|---|---|---|
| EP | 0547358 A3 | 10/1993 |
| EP | 1031328 A1 | 8/2000 |
| EP | 1844736 A1 | 10/2007 |
| WO | 9626748 A2 | 9/1996 |
| WO | 2004034913 A1 | 4/2004 |
| WO | 2006102573 A1 | 9/2006 |
| WO | 2010024871 A1 | 3/2010 |
| WO | 2010065030 A1 | 6/2010 |

OTHER PUBLICATIONS

Extended European Search Report for European Application No. 11848939.2, dated Aug. 10, 2017, 10 pages.

First Examiner's Report for Australian Application No. 2016203384, dated Jun. 1, 2018, 5 pages.

Acconcia, et al, "'Sutureless' Vesicourethral Anastomosis in Radical Retropubic Prostatectomy", The American Journal of Urology Review, Mar./Apr. 2003, vol. 1, No. 2, pp. 93-96.

Chancellor, at al, "Intraoperative Endo-Luminal Ultrasound Evaluation of Urethral Diverticula", The Journal of Urology, vol. 153, Jan. 1895, pp. 72-75.

Crook, et al, "Factors influencing risk of acute urinary retention after TRUS-guided permanent prostate seed implantation", Int. J. Radiation Oncology Biol. Phys., vol. 52, No. 2, 2002, pp. 453-460.

Diederich, et al, "Catheter-based ultrasound applicators for selective thermal ablation: progress towards MRI-guided applications in prostate", Int. J. Hyperthermia, vol. 20, No. 7, Nov. 2004, pp. 739-756.

Igel, et al, "Comparison of Techniques for Vesicourethral Anastomosis: Simple Direct Versus Modified Vest Traction Sutures", Urology, vol. 31, No. 6, Jun. 1988, pp. 474-477.

Lee, et al, "Dosimetric Consequences of Using a Surrogate Urethra to Estimate Urethral Dose After Brachytherapy for Prostate Cancer", Int. J. Radiation Oncology Biol. Phys., vol. 57, No. 2, 2003, pp. 355-361.

Merrick, et al, "Phophylactic Versus Therapeutic Alpha-Blockers After Permanent Prostate Brachytherapy", Urology 60 (4), 2002, pp. 650-655.

Ross, et al, "Highly Directional Transurethral Ultrasound Applicators with Rotational Control for MRI-Guided Prostatic Thermal Therapy", Phys. Med. Biol. 49, 2004, pp. 189-204.

Ryu, et al, "MRI Imaging of the Male and Female Urethra", Radiographics, Sep.-Oct. 2001, pp. 1169-1185.

Vaidyanathan, et al, "A Simple Radiological Technique for Demonstralion of Incorrect Positioning of a Foley Catheter with Balloon Inflated in the Urethra of a Male Spinal Cord Injury Patient", Scientific Word Journal, Jun. 20, 2006, pp. 2445-2449.

Zlotta, et al, "Percutaneous Transperineal Radiofrequency Ablation of Prostate Tumor: Safety, Feasibility and Pathological Effects on Human Prostate Cancer", British Journal of Urology, vol. 81, Feb. 1998, pp. 265-275.

Zelefsky, "Postimplantation Dosimetric Analysis of Permanent Transperineal Prostate Implantation: Improved Does Distributions with an Intraoperative Computer-Optimized Conformal Planning Technique", Int. J. Radiation Oncology Biol. Phys., vol. 48, No. 2, 2000, pp. 601-608.

* cited by examiner

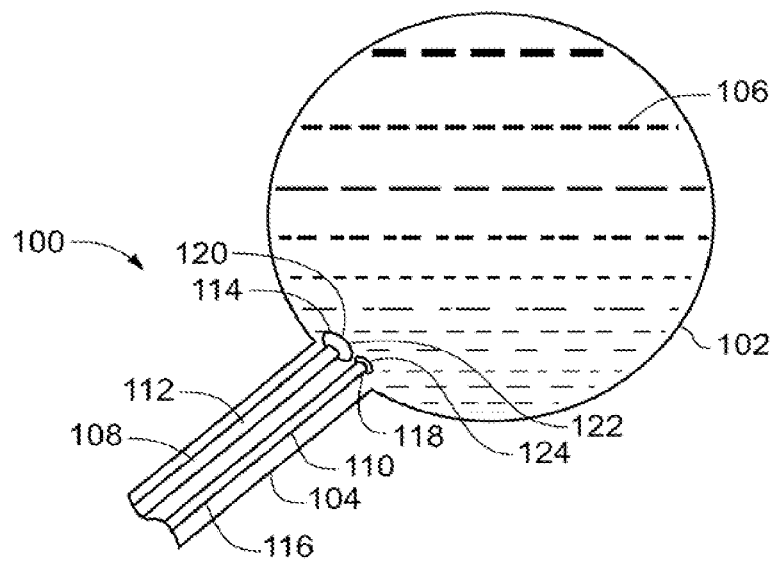
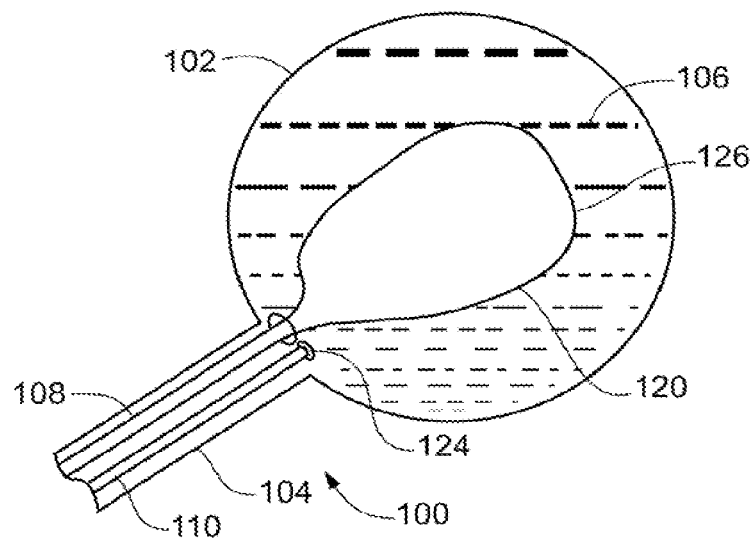

MICRO-NEEDLE BLADDER BALLOON

CROSS-REFERENCE TO RELATED APPLICATIONS

This application is a continuation of, and claims priority to, U.S. patent application Ser. No. 13/993,752, filed on Aug. 26, 2013, entitled "MICRO-NEEDLE BLADDER BALLOON", which is a National Phase entry of PCT Application No. PCT/US2011/065468, filed on Dec. 16, 2011, which claims priority from U.S. Provisional Application No. 61/423,732, filed on Dec. 16, 2010, the disclosures of which are incorporated by reference herein in their entirety.

FIELD OF THE INVENTION

The invention relates generally to urinary disorder treatment tools and methods. More specifically, the present invention is directed to a device, system and method of introducing stem cells to a patient's bladder tissue using an inflation balloon having a plurality of micro-needles.

BACKGROUND OF THE INVENTION

Urinary incontinence is a significant health concern worldwide. For example, lower urinary tract disorders affect the quality of life of millions of men and women in the United States every year. These disorders include overactive bladder. Overactive bladder is a treatable medical condition that is estimated to affect 17 to 20 million people in the United States. Current treatments for overactive bladder include medication, diet modification, programs in bladder training, electrical stimulation, and surgery. There is a continuing desire to provide additional treatment options that can be used as an alternative to, or in conjunction with, the current treatment options.

SUMMARY OF THE INVENTION

The present invention relates generally to devices and method for delivering treatment fluids or particulates such as, stem cells, drugs, Botox and like, to an inner lining of a bladder for treatment of urinary tract disorders, including over-active bladder. In the various embodiments, an inflation balloon includes micro-needles configured to pierce and otherwise puncture the inner bladder walls so as to deliver the treatment fluid to bladder tissue. Various embodiments of the invention allow the treatment fluid to be injected into the bladder tissue using the micro needles. Alternatively, the micro needles can be fabricated of bioabsorbable or bioresorbable materials such that the micro needles can remain embedded within the bladder tissue to deliver the treatment fluid or particulate.

In one aspect of the present invention, a balloon delivery system can comprise an inflation balloon fabricated so as to include a plurality of micro needles attached to an exterior surface of the inflation balloon. Following placement of the inflation balloon within the bladder, the inflation balloon can be fully inflated so as to come into contact with an inner wall of the bladder such that tips of the micro needle come into contact, pierce and enter the bladder tissue. Once embedded within the bladder tissue, a treatment fluid is delivered into the bladder tissue. In some embodiments, an internal inflation balloon can be inflated to pressurize the treatment fluid and otherwise force the inflation fluid through the micro needles for injection into the bladder tissue. In some embodiments, the micro needles can be formed of a bioabsorbable or bioresorbable material wherein the micro needles include barbs such the micro needles break off and remain embedded within the bladder tissue upon deflation of the inflation balloon. In some embodiments, the micro needles can be included on an internal inflation balloon that upon inflation, pierce a second inflation balloon that is in contact with the inner bladder wall, prior to the micro needles contacting and piercing the inner bladder wall. In some embodiments, the micro needles can be formed using the material of the inflation balloon.

In another aspect of the present invention, a balloon delivery system can include a lead structure that is introduced to the bladder within an inflation balloon. The lead structure can comprise a lead lumen that is fluidly connected to a central lead hub. A plurality of micro needles can be fluidly connected to the lead hub using individual flexible delivery tubes. The lead structure can be advanced through a catheter body such that the lead hub is positioned within the inflation balloon. Treatment fluid can be directed into the lead lumen, whereby the pressure of the treatment fluid causes the micro needles to deploy outwardly from the lead hub. As each micro needle approaches the inflation balloon, the pressure of the treatment fluid causes the micro needle to sequentially puncture the inflation balloon and internal bladder wall such that the micro needle can inject the treatment fluid into the bladder tissue. Following injection of the treatment fluid, the lead structure can be withdrawn from the inflation balloon.

In another aspect of the present invention, a balloon delivery system can include an inflation balloon wherein an exterior surface of the inflation balloon has been modified to from micro needles from the material of the inflation balloon itself. In some embodiments, a plurality of raised dimples can be formed in the exterior surface wherein each dimple defines a micro needle capable of piercing or otherwise puncturing an inner bladder wall for delivery of a treatment fluid to bladder tissue. In some embodiments, the exterior surface can include a plurality of recessed portions including a micro needle that can be deployed outwardly and into the inner bladder wall under the influence of a pressurized treatment fluid. In some embodiments, an internal inflation balloon can be utilized to pressurize the treatment fluid. The internal inflation balloon can include one or more well for storing the treatment fluid prior to its injection through the micro needles.

The above summary of the various representative embodiments of the invention is not intended to describe each illustrated embodiment or every implementation of the invention. Rather, the embodiments are chosen and described so that others skilled in the art can appreciate and understand the principles and practices of the invention. The figures in the detailed description that follow more particularly exemplify these embodiments.

BRIEF DESCRIPTION OF THE DRAWINGS

The invention can be completely understood in consideration of the following detailed description of various embodiments of the invention in connection with the accompanying drawings, in which:

FIG. 1 is a schematic representation of a urinary tract system including an inflation balloon catheter and drain catheter positioned therein FIG. 2 is a schematic representation of a urinary tract system including a partially inflated inflation balloon and drain catheter positioned therein.

Figure 3:
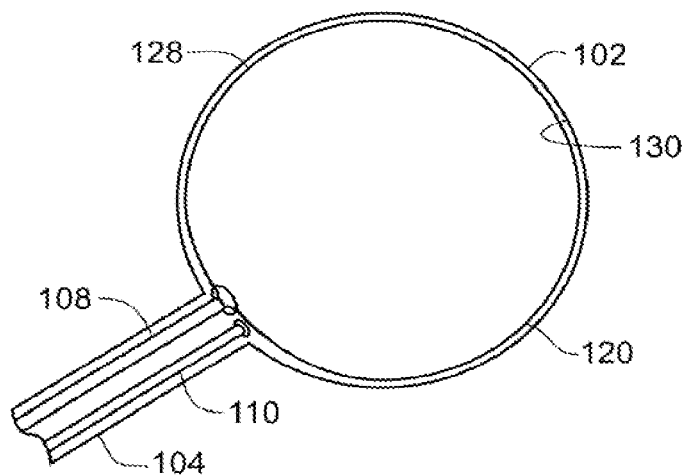
FIG. 3 is a schematic representation of a urinary tract system including a fully inflated inflation balloon and drain catheter positioned therein.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF PREFERRED EMBODIMENTS

The present invention is directed to devices, instruments, assemblies and methods for delivering an injectable treatment such as, for example, stem cells or medicants such as Botox and the like, to an inner lining of the bladder for treatment of urinary tract disorders, including over-active bladder (OAB).

As illustrated in FIG. 1, a urinary tract 100 of a representative individual includes a bladder 102 that is fluidly connected with a urethra 104. Bladder 102 generally accumulates a bodily fluid 106, i.e. urine that flows through urethra 104 prior to being discharged from the body. As illustrate, a balloon catheter 108 and a drain catheter 110 have been slidingly positioned within the urinary tract 100. Balloon catheter 108 generally includes a catheter body 112 defined between a distal treatment end 114 and a proximal biasing end (not shown) that remains external to the patient's body. Drain catheter 110 generally includes a drain catheter body 116 having a distal draining end 118 and a proximal draining end (not shown) that remains external to the patient's body. Attached to the distal treatment end 114 of the balloon catheter 108 is an inflation balloon 120. Generally, inflation balloon 120 is inserted into the urinary tract 100 with the inflation balloon 120 in an uninflated disposition 122. Drain catheter 110 is generally inserted such that a drain lumen 124 is positioned just inside the bladder 102.

As illustrated in FIG. 2, inflation balloon 120 can begin to be inflated to a partially inflated disposition 126 utilizing an inflation fluid such as saline or air that is introduced through the balloon catheter 108. As the inflation balloon 120 is inflated, bodily fluid 106 is expelled from the bladder 102 through the drain lumen 124 whereby the bodily fluid 106 travels through the drain catheter 110 and out the urinary tract 100. As illustrated in FIG. 3, inflation balloon 120 is eventually inflated to a fully inflated disposition 128 wherein the inflation balloon 120 is in direct contact with an inner bladder wall 130 and all of the bodily fluid 106 has been evacuated from bladder 102. For purposes of clarity, the Figures generally show a gap between the inflation balloon 120 and the inner bladder wall 130 though it is to be understood that in practice, the inflation balloon 120, when inflated to fully inflated disposition 128, will be in direct physical contact with the inner bladder wall 130.

Figure 4:
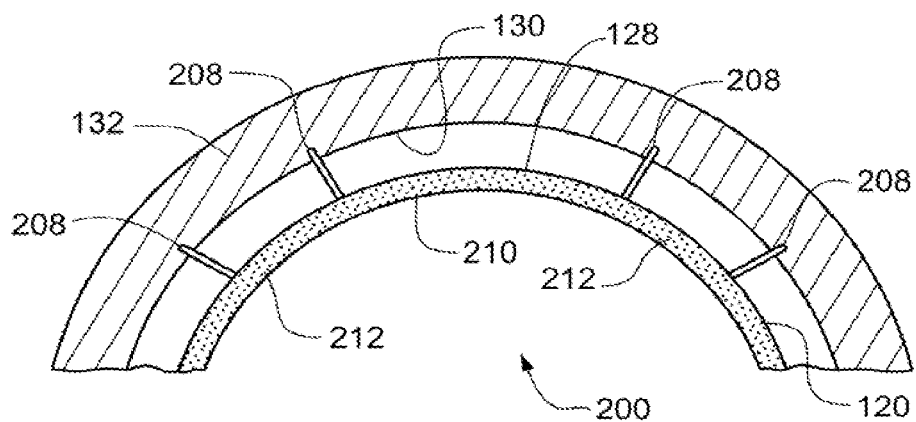
FIG. 4 is a partial section view of a balloon delivery system according to an embodiment of the present invention.
Figure 5:
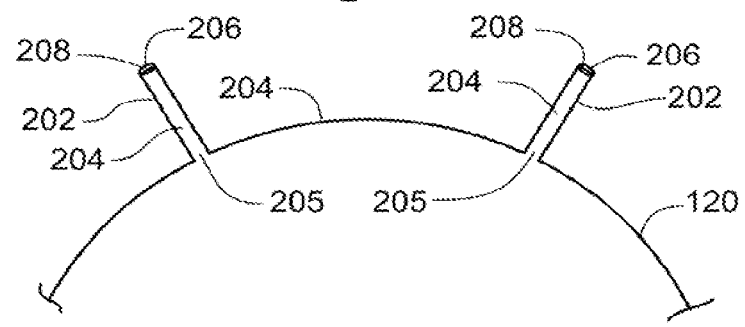
FIG. 5 is a partial side view of an inflation balloon for use with the balloon delivery system of FIG. 4.

Referring now to FIGS. 4 and 5, a representative balloon delivery system 200 of the present invention can comprise inflation balloon 120 including a plurality of micro needles 202 attached to an exterior balloon surface 204 of the inflation balloon 120. Each micro needle 202 generally includes an injection lumen 204 defined between an inlet aperture 205 and an injection aperture 206 located at a needle tip 208. Balloon delivery system 200 can further comprise an internal inflation balloon 210 that is located internal to the inflation balloon 120, wherein operation of the internal inflation balloon 210 is independent of the inflation of inflation balloon 120.

In using representative balloon delivery system 200, inflation balloon 120 is fully inflated while any bodily fluid 106 is evacuated from the bladder 102. As inflation balloon 120 approaches fully inflated disposition 128, each needle tip 208 begins to contact the inner bladder 25 wall 130 such that when inflation balloon 120 achieves the fully inflated disposition 128, each needle tip 128 has punctured or otherwise perforated the inner bladder wall 130 with the injection aperture 206 being fully imbedded within bladder tissue 132. Next, a treatment fluid 212 can be introduced into the inflation balloon 120 through the catheter body 112. Treatment fluid 212 can include a variety of treatment modalities including, for example, stem cells, drugs and medicants such as Botox. With the treatment fluid 212 introduced to the inflation balloon 120, internal inflation balloon 210 can be advanced into the inflation balloon 120 through the catheter body 112. Internal inflation balloon 210 generally includes its own inflation lumen such that internal inflation balloon 210 can be individually inflated within inflation balloon 120. As internal inflation balloon 210 is inflated, treatment fluid 212 which is present between the inflation balloon 120 and internal inflation balloon 210 is pressurized such the treatment fluid 212 enters each inlet aperture 205 for subsequent injection into the bladder tissue 132. As internal inflation balloon 210 approaches a fully inflated state in which the internal inflation balloon 210 contacts the inflation balloon 120, all of the treatment fluid 212 is forcibly directed into the bladder tissue 132 through the micro needles 202. The rate of delivery of treatment fluid 212 through the micro needles 202 can be controlled by decreasing or increasing the pressure in the internal inflation balloon 210. In some representative embodiments, each injection lumen 204 can have a diameter of at least about 0.337 mm and can be capable of delivering 30 mL of treatment fluid 212.

Figure 6:
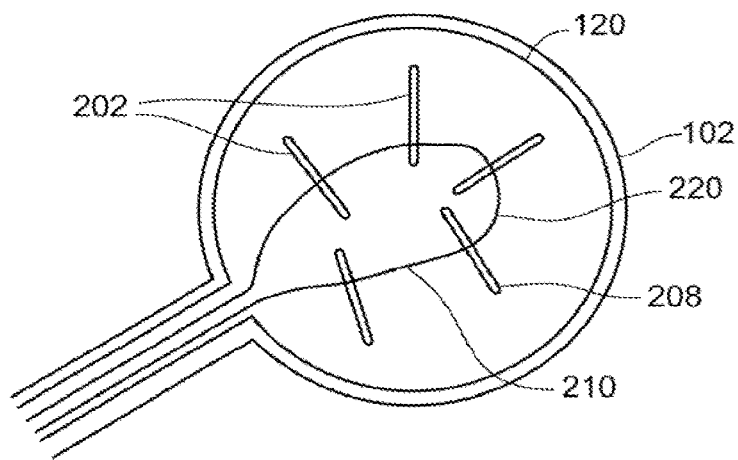
FIG. 6 is a schematic representation of a balloon delivery system according to an embodiment of the present invention.
Figure 7:
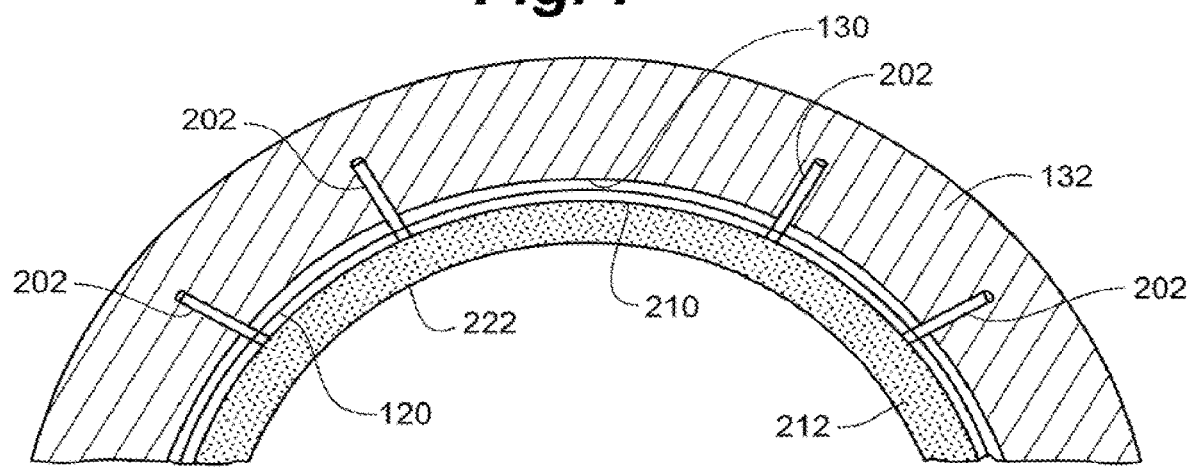
FIG. 7 is a partial section view of the balloon delivery system of FIG. 6.

In a variation of balloon delivery system 200 as illustrated in FIGS. 6 and 7, the micro needles 202 can be operably coupled to an exterior surface 220 of the internal inflation balloon 210. Once again, inflation balloon 120 is fully inflated to evacuate any bodily fluid 106 from the bladder 102. With inflation balloon 120 in fully inflated disposition 128 and in direct contact with inner bladder wall 130, internal inflation balloon 210 can be advanced into the inflation balloon 120. Internal inflation balloon 210 can then be inflated causing the micro needles 202 to approach and ultimately puncture the inflation balloon 120 and inner bladder wall 130 such that each needle tip 208 enters the bladder tissue 132. Treatment fluid 212 can be introduced into the internal inflation balloon 210 wherein a third internal inflation balloon 222 can be inserted into internal inflation balloon 210. Inflation of the third internal inflation balloon 222 causes treatment fluid 212 to become pressurized such that it is then forcibly directed into the bladder tissue 132 through the micro needles 202.

Figure 8:
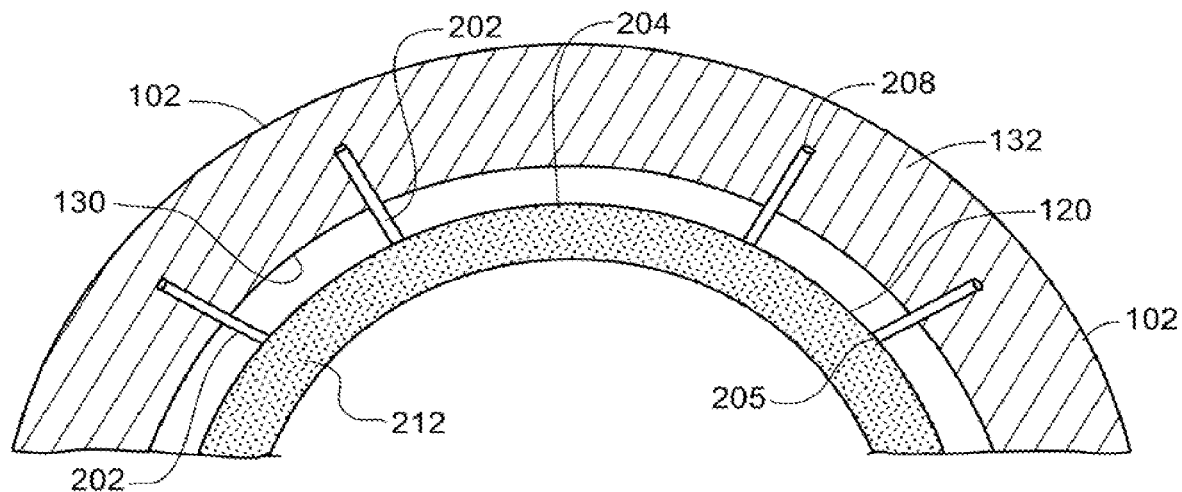
FIG. 8 is a partial section view of a balloon delivery system according to an embodiment of the present invention.

In a variation of balloon delivery system 200 as illustrated in FIG. 8, inflation balloon 120 can be constructed such that micro needles 202 are constructed to require a minimum injection pressure prior to treatment fluid 212 entering the inlet aperture 205. For instance, a diameter of the injection lumen 204 may necessitate a certain fluid pressure be achieved before a surface tension of treatment fluid 212 is exceeded, whereby the treatment fluid 212 can enter the inlet aperture 205.

Once again, inflation balloon 120 is fully inflated while any bodily fluid 106 is evacuated from the bladder 102. As the inflation balloon 120 approaches fully inflated disposition 128, each needle tip 208 begins to contact the inner bladder wall 130 such each needle tip 128 punctures or otherwise perforates the inner bladder wall 130 with the injection aperture 206 being fully imbedded within bladder tissue 132. Treatment fluid 212 can be directly introduced into the inflation balloon 120 through the catheter body 112, whereby the treatment fluid 212 can be pressurized to exceed the minimum injection pressure and injection of the treatment fluid 212 into the bladder tissue 132 can be accomplished.

Figure 9:
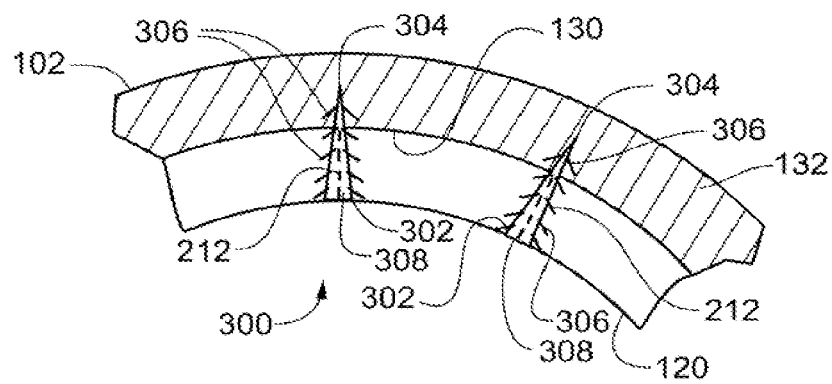
FIG. 9 is a partial section view of a balloon delivery system according to an embodiment of the present invention.
Figure 10:
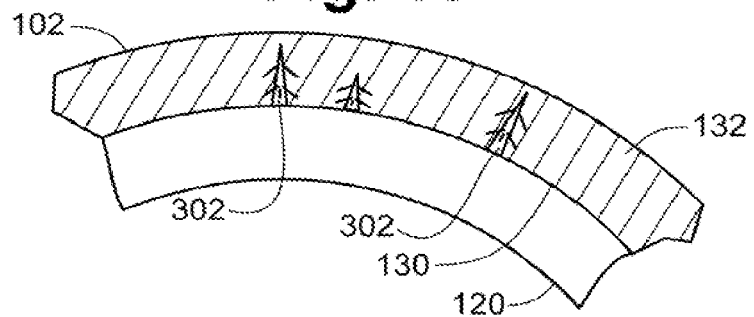
FIG. 10 is a partial section view of the balloon delivery system of FIG. 9.

In an alternative embodiment of a balloon delivery system 300 as illustrated in FIGS. 9 and 10, inflation balloon 120 can comprise a plurality of barbed micro needles 302. Each barbed micro needle 302 can comprise an insertion tip 304 and a plurality of individual barbs 306. Barbed micro needle 302 can be generally formed of a bioabsorbable or bioresorbable material such as, for example, polymers and copolymers of polylactides, polyglycolides and like. Barbed micro needle 302 is generally molded from the bioabsorbable or bioresorbable material and can be overmolded, insert molded or otherwise attached to the inflation balloon 120 during fabrication of the inflation balloon 120. Barbed micro needle 302 can include an internal reservoir 308 for retaining an amount of the treatment fluid 212. Alternatively, treatment fluid 212 can be included within the bioabsorbable or bioresorbable material during forming of the barbed micro needle 302. In some embodiments, treatment fluid 212 can be replaced with a treatment particulate that is molded into the barbed micro needle 302.

With balloon delivery system 300, the inflation balloon 120 is fully inflated while any bodily fluid 106 is evacuated from the bladder 102. As the inflation balloon 120 approaches fully inflated disposition 128, the insertion tip 304 of each barbed micro needle 302 begins to contact the inner bladder wall 130 such that when inflation balloon 120 is in fully inflated disposition 128, the barbed micro needle 302 including the barbs 306 is fully embedded within bladder tissue 132. Next, the inflation fluid within the inflation balloon 120 can be removed thereby causing inflation balloon 120 to retract and return to the uninflated disposition 122. As the inflation balloon 120 deflates, the barbs 306 resist the removal of the barbed micro needles 302 from within bladder tissue 132 such that ultimately, each barbed micro needle 302 breaks off and separates form the inflation balloon 120. As such, each barbed micro needle 302 remains embedded within the bladder tissue 132 such that the treatment fluid 212, or solid treatment particulates, are administered during the time period in which the bioabsorbable or bioresorbable materials are broken down by the body.

Figure 11:
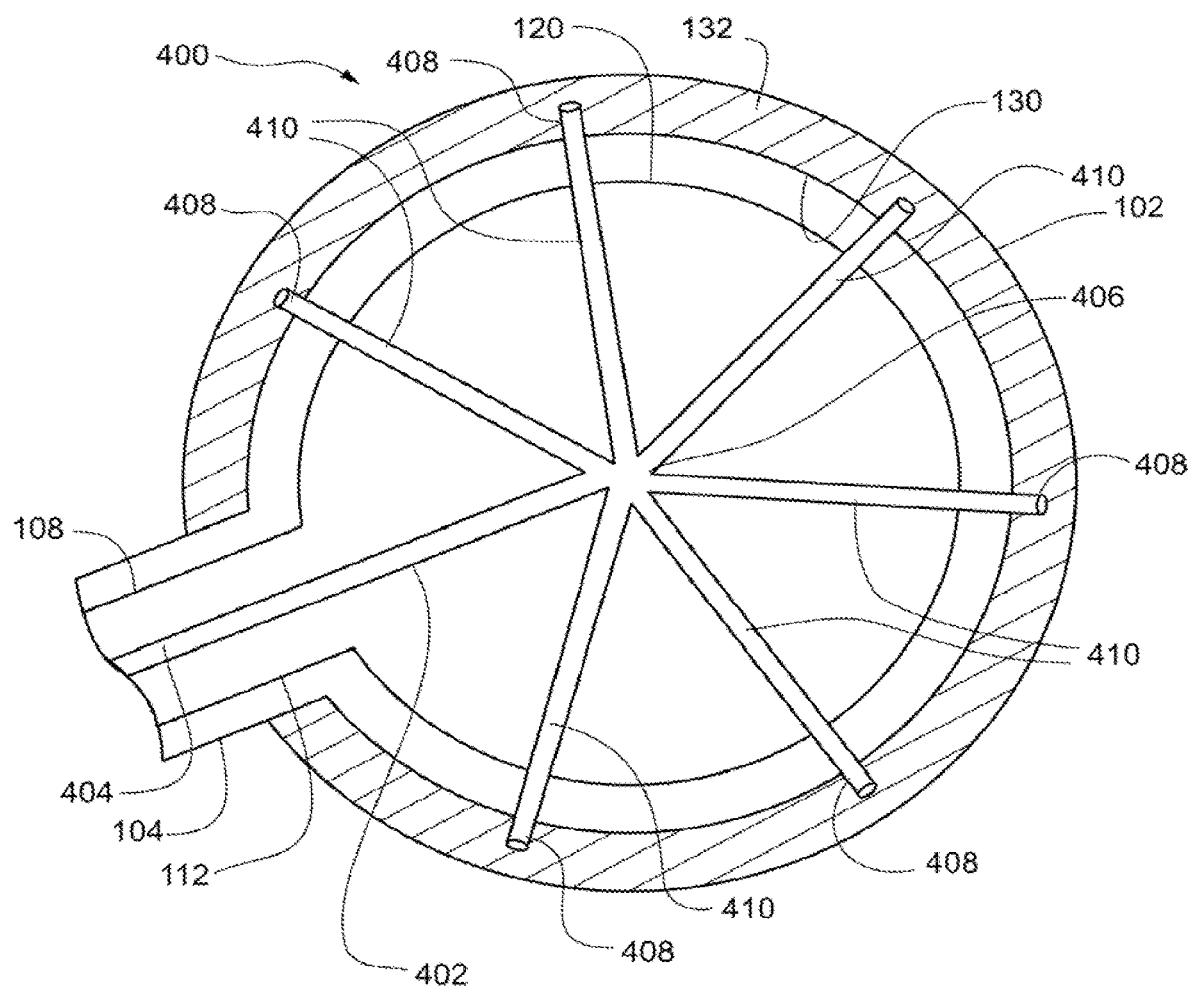
FIG. 11 is a schematic representation of a balloon delivery system according to an embodiment of the present invention.
Figure 12:
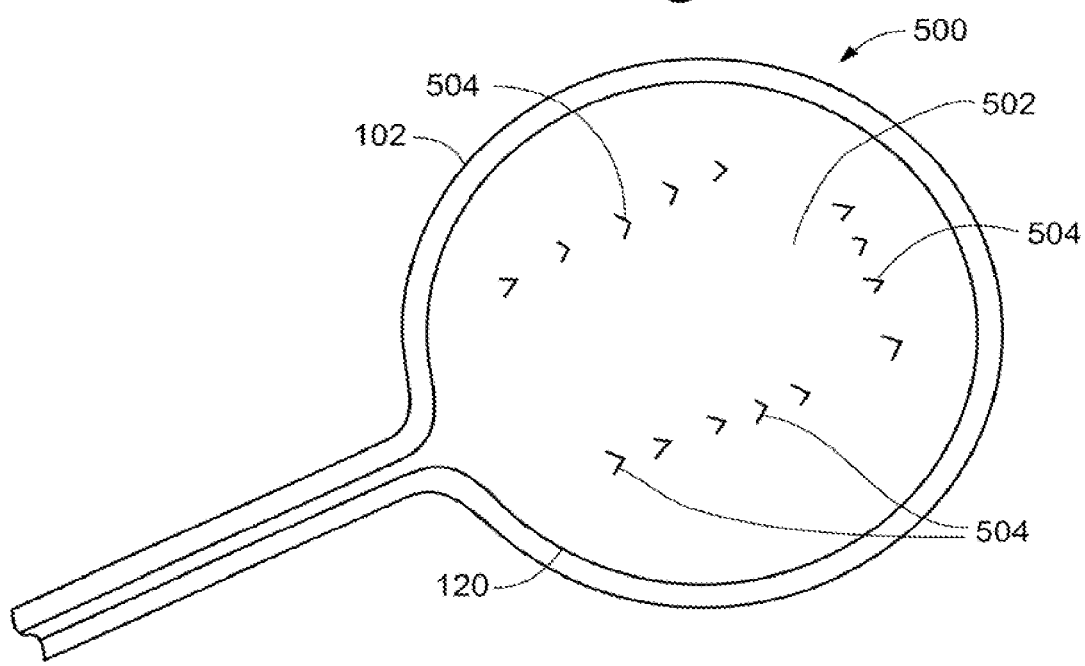
FIG. 12 is a schematic representation of a balloon delivery system according to an embodiment of the present invention.
Figure 13:
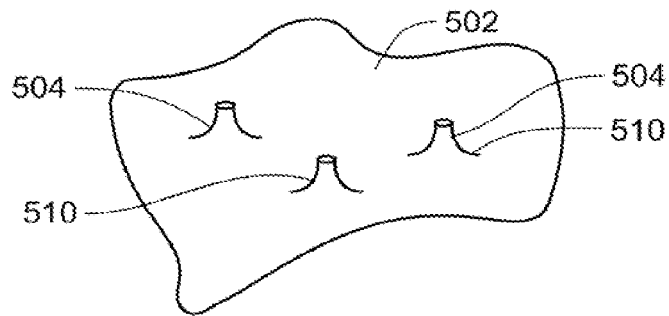
FIG. 13 is a perspective view of a portion of an inflation balloon for use with the balloon delivery system of FIG. 12.

In an alternative embodiment of a balloon delivery system 400 as illustrated in FIG. 11, the balloon delivery system can include a lead structure 402 that is ultimately introduced inside inflation balloon 120. Generally, the lead structure 402 can include a lead lumen 404 that is fluidly connected to a lead hub 406. A plurality of micro needles 408 are fluidly connected to the lead hub 406 with flexible delivery tubes 410.

Generally, the inflation balloon 120 can be advanced into the bladder 102 and inflated to the fully inflated disposition 128 such that all of the bodily fluid 106 has been evacuated from within bladder 102. Lead structure 402 can be advanced through the catheter body 112 such that the lead hub 406 is located within the inflation balloon 120. Treatment fluid 112 can then be directed into the lead lumen 404, whereby the pressure of the treatment fluid 112 causes the micro needles 408 to deploy outwardly from the lead hub 406. As each micro needle 408 approaches the inflation balloon 120, the pressure of the treatment fluid 112 causes the micro needle 408 to sequentially puncture the inflation balloon 120 and internal bladder wall 130 such that the micro needle 408 can inject the treatment fluid 112 into the bladder tissue 132. Following injection of the treatment fluid 112, the lead structure 102 can be withdrawn from the inflation balloon 120.

Figure 14:
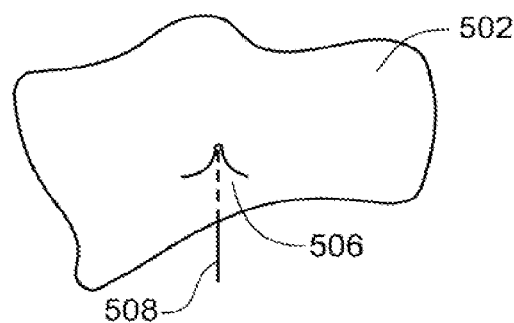
FIG. 14 is a perspective view of the inflation balloon of FIG. 13.
Figure 15:
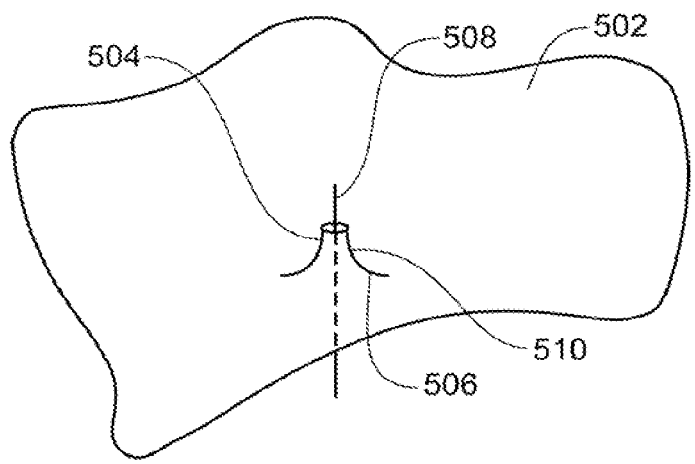
FIG. 15 is a perspective view of the inflation balloon of FIG. 13.
Figure 16:
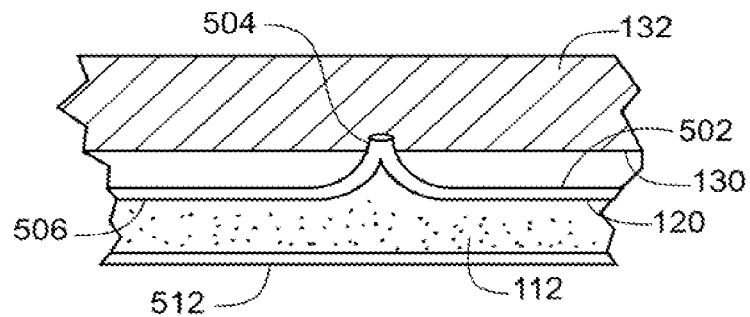
FIG. 16 is a partial section view of the balloon delivery system of FIG. 12.

In another alternative embodiment of a balloon delivery system 500 as illustrated in FIGS. 12, 13, 14 and 15, inflation balloon 120 can include an exterior surface 502 that is manipulated to form a plurality of micro needles 504 from the balloon material itself. As seen in FIGS. 14 and 15, inflation balloon 120 can include an interior surface 506 into which a needle 508 is directed into, wherein the needle 508 is as advanced through the inflation balloon 120 and out the exterior surface 502. As the needle 508 is pulled from the exterior surface 502, a raised dimple 510 is created that ultimately forms the micro needles 504. Preferably, the inflation balloon 120 is fabricated of a generally stiff material such that raised dimples 502 and micro needles 504 are capable of puncturing the inner bladder wall 130. Once again, the inflation balloon 120 can be inflated such that the micro needles 504 are in contact and ultimately puncture the bladder wall 130 as shown in FIG. 16. Treatment fluid 112 within the inflation balloon 120 can be pressurized with an internal inflation balloon 512 such that the treatment fluid 112 is injected into the bladder tissue 132 through micro needles 504.

Figure 17:
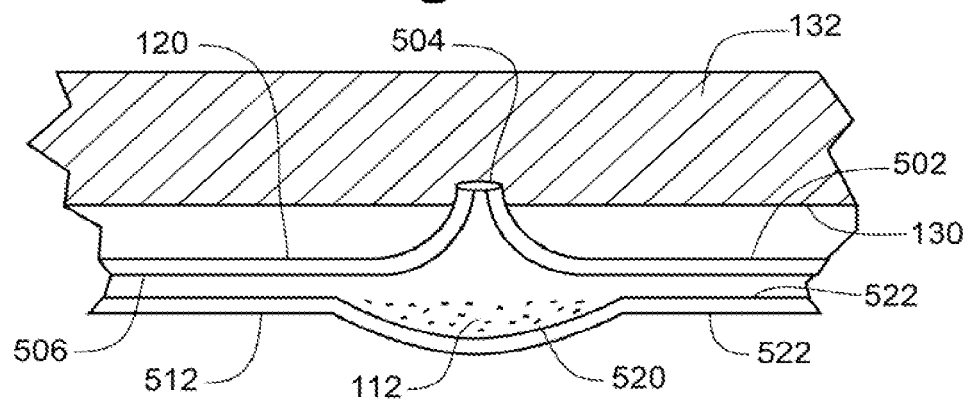
FIG. 17 is a partial section view of the balloon delivery system of FIG. 12.

In a variation of balloon delivery system 500, the treatment fluid 112 can be stored or otherwise provided in a plurality of wells 520 arranged about an exterior surface 522 of the internal inflation balloon 512 as shown in FIG. 17. Once the inflation balloon 120 has been fully inflated such that the micro needles 504 have puncture the inner bladder wall 130, the internal inflation balloon 512 can be inflated such that as the internal inflation balloon 512 reaches a fully inflated state, the treatment fluid 512 is ejected from the wells 520 for injection through the micro needles 504.

Figure 18:
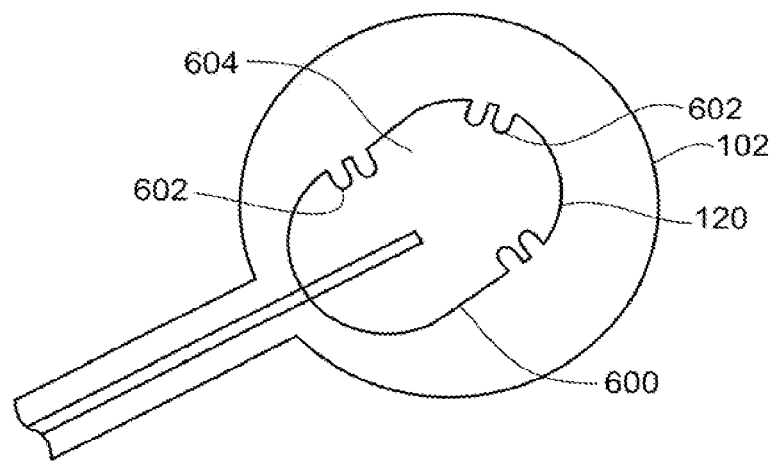
FIG. 18 is a schematic representation of a balloon delivery system according to an embodiment of the present invention.
Figure 19:
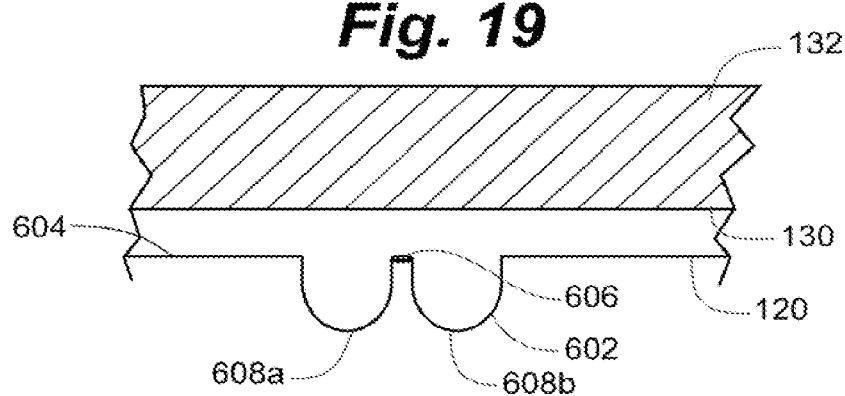
FIG. 19 is a partial section view of the balloon delivery system of FIG. 18.
Figure 20:
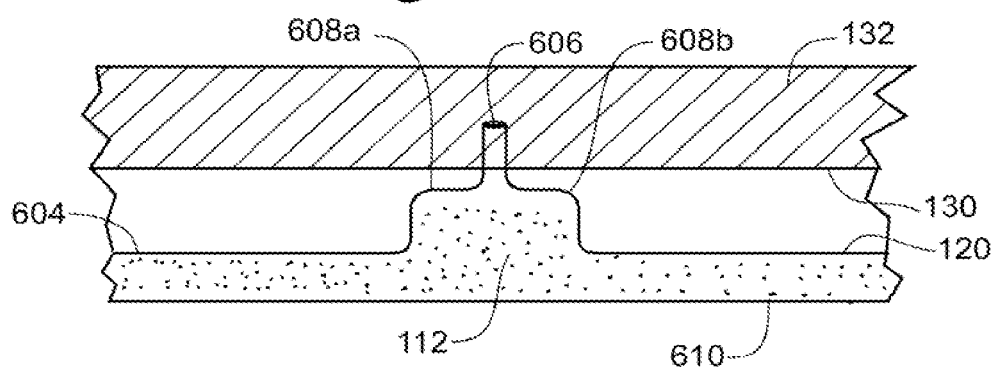
FIG. 20 is a partial section view of the balloon delivery system of FIG. 18.

In another alternative embodiment of a balloon delivery system 600, an inflation balloon 120 can include a plurality or recessed areas 602 defined in an exterior balloon surface 604 as shown in FIGS. 18, 19 and 20. Each recessed area 602 can include a micro needle 606 and a pair of hinge portions 608a, 608b. Generally, inflation balloon 120 is inserted into bladder 102 wherein the inflation balloon 120 can be inflated to come into contact with the inner bladder wall 130. An internal inflation balloon 610 can then be inserted into the inflation balloon 120 and inflated such that as the internal inflation balloon 610 reaches a fully inflated state, treatment fluid 112 becomes pressurized. The pressure of treatment fluid 112 causes the hinge portions 608a, 608b to transition such that the recessed area 602 is pushed toward the inner bladder wall 130. As the recessed area 602 is pushed outward, the micro needle 606 pierce and puncture in the inner bladder wall 130 and becomes embedded within the bladder tissue 132 whereby the treatment fluid 112 is injected into the bladder tissue 132 through micro needle 606.

Although specific examples have been illustrated and described herein, it will be appreciated by those of ordinary skill in the art that any arrangement calculated to achieve the same purpose could be substituted for the specific examples shown. This application is intended to cover adaptations or variations of the present subject matter. Therefore, it is intended that the invention be defined by the attached claims and their legal equivalents, as well as the following illustrative embodiments.

What is claimed is:

1. A balloon delivery system for delivering a treatment fluid to bladder tissue, comprising:
 a balloon catheter including a catheter body having a distal treatment end, the distal treatment including an inflation balloon, the balloon catheter including a lead lumen operatively coupled to a hub disposed within the inflation lumen, and
 a plurality of micro needles operatively coupled to the hub, each micro needle including a lumen and a needle tip configured to puncture an inner bladder wall for delivery of a treatment medicant into bladder tissue, each micro needle puncturing the inner bladder wall when an inflation balloon is disposed in an inflated disposition.

2. The balloon delivery system of claim 1, wherein the plurality of micro needles are formed directly on an exterior surface of the inflation balloon.

3. A balloon delivery system for delivering a treatment fluid to bladder tissue, comprising:
 a balloon catheter including a catheter body having a distal treatment end, the distal treatment end including a first inflation balloon;
 an second inflation balloon positioned within the inflation balloon;
 a third inflation balloon; and
 a plurality of micro needles formed on an exterior surface of the second inflation balloon, each micro needle defining a lumen and including a needle tip configured to puncture an inner bladder wall when the second inflation balloon is disposed in in an inflated disposition, wherein the treatment fluid is located between the second inflation balloon and the third inflation balloon such that inflation of the third inflation balloon directs the treatment fluid through the micro needles and into the inner bladder wall.

4. The balloon delivery system of claim 3, wherein each micro needle is defined within a recessed area on the exterior surface, the recessed area further comprising a pair of hinges with a hinge on each side of the micro needle, wherein inflation of the second inflation balloon causes each recessed area to be directed outward with the pair of hinges directing each micro needle into the inner bladder wall.

5. The balloon delivery system of claim 3, wherein each micro needle comprises a stiff dimple formed by passing a needle through an interior surface of the first inflation balloon and out the exterior surface such that said stiff dimple punctures the inner bladder wall with the second inflation balloon is disposed in the inflated disposition.

6. The balloon delivery system of claim 3, wherein each micro needle is fabricated of a bioabsorbable or bioresorbable polymer and wherein each micro needle comprises a plurality of barbs such that each barb becomes embedded in the inner bladder wall with the second inflation balloon in a fully inflated disposition and whereupon said plurality of barbs retain each micro needle within the inner bladder wall as the second inflation balloon is deflated and assumes an uninflated disposition causing each micro needle to break off of the exterior surface of the second inflation balloon.

7. The balloon delivery system of claim 6, wherein the treatment fluid is administered into bladder tissue during a time period in which the bioabsorbable or bioresorbable polymer is broken down by the bladder tissue.

8. The balloon delivery system of claim 6, wherein each micro needle includes an internal reservoir for retaining the treatment fluid.

9. The balloon delivery system of claim 6, wherein the treatment fluid is included within the bioabsorbable or bioresorbable polymer during formation of each micro needle.

10. The balloon delivery system of claim 3, wherein the second inflation balloon includes a plurality of wells arranged on an exterior surface with the treatment fluid stored in the plurality of wells such that upon the second inflation balloon reaching a fully inflated state, the treatment fluid is ejected from the plurality of wells for injection of the treatment fluid through the plurality of micro needles.

11. The balloon delivery system of claim 3, wherein said plurality of micro needles are formed directly on the second inflation balloon, wherein inflation of the second inflation balloon directs the micro needles to puncture the first inflation balloon as each micro needle is directed into the inner bladder wall.

12. The balloon delivery system of claim 3, wherein inflation of the second inflation balloon pressurizes the treatment fluid.

13. A balloon delivery system for delivering a treatment fluid to bladder tissue, comprising:
  a balloon catheter including a catheter body having a distal treatment end, the distal treatment end including an inflation balloon; and
  a lead structure positioned inside the inflation balloon, the lead structure including a lead lumen fluidly connected to a lead hub, the lead hub further comprising a plurality of flexible delivery tubes fluidly connected to the lead hub, the lead structure including a plurality of micro needles where each micro needle is fluidly attached to a flexible delivery tube.

14. The balloon delivery system of claim 13, wherein delivery of the treatment fluid through the lead lumen and into the lead hub directs the micro needles to deploy outwardly from the lead hub so as to puncture the inner bladder wall and wherein the treatment fluid is delivered through each flexible delivery tube such that the treatment fluid is injected through each micro needle and into the inner bladder wall.

* * * * *